US010258649B2

(12) United States Patent
Klingemann et al.

(10) Patent No.: US 10,258,649 B2
(45) Date of Patent: Apr. 16, 2019

(54) TUMORICIDAL AND ANTIMICROBIAL COMPOSITIONS AND METHODS

(71) Applicant: NantKwest, Inc., Culver City, CA (US)

(72) Inventors: Hans G. Klingemann, Culver City, CA (US); Barry J. Simon, Culver City, CA (US)

(73) Assignee: NANTKWEST, INC., San Diego, CA (US)

( * ) Notice: Subject to any disclaimer, the term of this patent is extended or adjusted under 35 U.S.C. 154(b) by 0 days.

(21) Appl. No.: 15/032,518

(22) PCT Filed: Oct. 28, 2014

(86) PCT No.: PCT/US2014/062695
§ 371 (c)(1),
(2) Date: Apr. 27, 2016

(87) PCT Pub. No.: WO2015/066054
PCT Pub. Date: May 7, 2015

(65) Prior Publication Data

US 2016/0250256 A1   Sep. 1, 2016

Related U.S. Application Data

(60) Provisional application No. 61/899,066, filed on Nov. 1, 2013.

(51) Int. Cl.
*A61K 35/17* (2015.01)
*A61K 9/00* (2006.01)
*C12N 5/0783* (2010.01)
*A61K 38/20* (2006.01)
*A01N 63/02* (2006.01)
*A61K 9/08* (2006.01)
*A61K 9/06* (2006.01)
*A61K 9/50* (2006.01)
*A61K 35/12* (2015.01)

(52) U.S. Cl.
CPC ............. *A61K 35/17* (2013.01); *A01N 63/02* (2013.01); *A61K 9/0014* (2013.01); *A61K 9/0019* (2013.01); *A61K 9/06* (2013.01); *A61K 9/08* (2013.01); *A61K 9/5068* (2013.01); *A61K 38/2013* (2013.01); *C12N 5/0646* (2013.01); *A61K 2035/124* (2013.01)

(58) Field of Classification Search
None
See application file for complete search history.

(56) References Cited

U.S. PATENT DOCUMENTS 7,618,817 B2  11/2009  Campbell
8,034,332 B2  10/2011  Klingemann
8,067,044 B2  11/2011  Henry et al.

8,313,943 B2   11/2012  Campbell
2004/0018183 A1  1/2004  Klingemann
2011/0003008 A1  1/2011  Lim

FOREIGN PATENT DOCUMENTS

JP    2008-505071 A    2/2008
WO   2006/004518 A1   1/2006

OTHER PUBLICATIONS

Reefman, Esther; et al; "Cytokine Secretion is Distinct from Secretion of Cytotoxic Granules in NK Cells" The Journal of Immunology, 184, 4852-4862, 2010 (Year: 2010).*
Tonn, Torsten; et al; "Cellular Immunotherapy of Malignancies Using the Clonal Natural Killer Cell Line NK-92" Journal of Hematotherapy & Stem Cell Research, 10, 535-544, 2001 (Year: 2001).*
Zhang, Bin; et al; "Comparison in the effects of IL-2, IL-12, IL-15 and IFNα on gene regulation of granzymes of human NK cell line NK-92" International Immunopharmacology, 8, 989-996, 2008 (Year: 2008).*
Connor, "Exclusive: Cancer—A cure just got closer thanks to a tiny British company—and the results could change lives of millions," Independent, News, Science, Jul. 13, 2013.
Choi et al., "Relapse in children with acute lymphoblastic leukemia involving selection of a preexisting drug-resistant subclone," Blood, 2007, 110:632-639.
Stoiser et al., "Prognosis of patients with a second relapse of acute myeloid leukemia," Leukemia, 2000, vol. 14, pp. 2059-2063.
Ki et al., "Bacterial skin and soft tissue infections in adults: A review of their epidemiology, pathogenesis, diagnosis, treatment and site of care," Can. J. Infect. Dis. Med, Microbiol. Mar. 2008; 19(2): 173-184.
Herberman et al., "Natural killer cells: their roles in defenses against disease," Science, Oct. 2, 1981; vol. 214, Issue 4516, pp. 24-30.
Melder et al., A New Approach to Generating Antitumor Effectors for Adoptive Immunotherapy Using Human Adherent Lymphokine-activated Killer Cells; Cancer Research 48, 3461-3469, Jun. 15, 1988.
Richards et al., "Human NK cells in health and disease: clinical, cunctional, phenotypic and DNA genotypic characteristics," Leuk Lymphoma, vol. 7, Issue 5-6, pp. 377-399, Aug. 1992.
Rosenberg et al., A Progress Report on the Treatment of 157 Patients with Advanced Cancer Using Lymphokine-Activated Killer Cells and Interleukin-2 or High-Dose Interleukin-2 Alone, New Engl. J. Med., vol. 316, pp. 889-897, Apr. 9, 1987.
Gong et al., "Characterization of a Human Cell Line (NK-92) with Phenotypical and Functional Characteristics of Activated Natural Killer Cells," Leukemia, Apr. 1994, 8(4):652-658.
Lugini et al., Immune Surveillance Properties of Human NK Cell-Derived Exosmes, J. Immunol. 2012; 189:2833-2842.

(Continued)

*Primary Examiner* — David W Berke-Schlessel
(74) *Attorney, Agent, or Firm* — Kilpatrick Townsend & Stockton LLP (57) ABSTRACT

Provided herein are pharmaceutical compositions comprising tumoricidal and/or antimicrobial components isolated from the supernatant of NK-92 cell medium and methods of using the compositions for killing cancer cells.

17 Claims, 4 Drawing Sheets

(56) References Cited

OTHER PUBLICATIONS

Rani et al., "Isolation of exosomes for subsequent mRNA, MicroRNA, and protein profiling," Methods Mol. Biol. 2011; 784:181-95.
Rosental et al., "A novel mechanism for cancer cells to evade immune attack by NK cells," OncoImmunology 1:4, 572-574, Jul. 2012.
Sahm et al., Expression of IL-15 in NK cells results in rapid enrichment and selective cytotoxicity of gene-modified effectors that carry a tumor-specific antigen receptor, Cancer Immunol. Immunother. 61:1451-1461, 2012.
PCT/US2014/062695, International Search Report dated Jan. 29, 2015.
Duck Cho et al.: "Expansion and Activation of Natural Killer Cells for Cancer Immunotherapy", Korean Journal of Laboratory Medicine, vol. 29, No. 2, Jan. 1, 2009, p. 89, XP055342587, KR ISSN: 1598-6535, DOI: 10.3343/jkjlm.2009.29.2.8.
Y. Liu, et al.: "Growth and Activation of Natural Killer Cells Ex Vivo from Children with Neuroblastoma for Adoptive Cell Therapy", Clinical Cancer Research, vol. 19, No. 8, Feb. 1, 2013, pp. 2132-2143, XP055342076. US ISSN: 1078-0432, DOI: 10.1158/1078-0432.CCR-12-1243.
EP Application No. 14858835.3, Extended European Search Report, dated Mar. 22, 2017, 8 pages.
Pores-Fernando et al, "Calcineurin dependent lytic granule exocytosis in NK-92 Natural Killer cells," Cell Immunol., 2009; 254(2), pp. 105-109; doi:10.1016/j.cellimm.2008.07.004.

\* cited by examiner

Nucleoporin = Nuclear membrane marker
Prohibitin = Mitochondrial marker
Rab5B = Exosomes marker

TUMORICIDAL AND ANTIMICROBIAL COMPOSITIONS AND METHODS

CROSS-REFERENCE TO RELATED APPLICATIONS

This application is a 35 USC § 371 national stage entry of International Application No. PCT/US2014/062695, filed Oct. 28, 2014, which claims the benefit of U.S. Provisional Application No. 61/899,066, filed Nov. 1, 2013, both of which are incorporated by reference herein in their entireties.

FIELD OF THE INVENTION

This invention relates generally pharmaceutical compositions having tumordical and/or antimicrobial properties and methods of using these compositions for killing cancer and/or microbes.

STATE OF THE ART

Skin cancer is the leading type of cancer in humans as well as many domesticated animals. The occurrence of skin cancer and melanomas are increasing significantly due to a variety of factors including exposure of unprotected skin to UV rays, such as those found in sunlight or tanning beds. When diagnosed at their incipient stage, these cancers are readily treatable by excision of the cancer and surrounding tissue. However, as in any surgical procedure, there remains the possibility that aberrant cancer cells may be retained at the site of the incision thereby causing recurrence of the cancer. This is particularly the case for melanomas, and the failure to remove all of the tumor can result in metastasis accompanied by high levels of morbidity.

There are numerous aggressive protocols that can be taken to minimize the risk of recurrence including conventional therapeutic protocols as well as numerous checkups with the attending clinician. Notwithstanding such protocols, melanomas tend to be very aggressive, and it is reported that melanoma has a 2% to 65% likelihood of recurrence within 5 years, depending on the stage of the cancer at treatment. See, e.g., www.aimatmelanoma.org/en/aim-for-answers/moving-on-after-treatment/follow-up-by-stage.html.

Animals are also prone to skin cancers, especially melanoma, squamous cell carcinoma, and mast cell tumors. Skin cancers are especially prevalent in animals that spend a lot of time in the sun.

Infections are a common problem throughout the world. Many infections are caused by bacteria, fungi, and other microbes. Although current treatment for such infections relies heavily on antibiotics and antimicrobial drugs, an increasing number of bacterial infections are found to be resistant to at least some antibiotics. The CDC reports that over two million Americans are infected by antibiotic-resistant microbes every year, resulting in more than 23,000 deaths. See, e.g., www.medicalnewstoday.com/articles/266182.php. Skin and soft tissue infections represent the third most common diagnosis in emergency care settings, and an estimated 7% to 10% of all hospitalized patients have a skin or soft tissue infection. Ki and Rotstein, Can. J. Infect. Dis. Med. Microbiol. 2008 March; 19(2): 173-184. Other common infections include systemic infections, respiratory infections, ear infections, gastrointestinal infections, and urinary tract infections. Infections are similarly common in domesticated animals and can be difficult to treat. Viral infections are also common, and few treatments are available for treating such infections.

Accordingly, there remains a need for tumorcidal compositions useful in lysing cancer cells, especially those related to dermal and subdermal cancers. There also remains a need for novel antimicrobial compositions useful in treating infection.

SUMMARY OF THE INVENTION

Certain cells of the immune system have cytotoxic activity against particular target cells. Natural killer (NK) cells, generally representing about 10-15% of circulating lymphocytes, bind and kill target cells, including virus-infected cells and many malignant cells, nonspecifically with regard to antigen and without prior immune sensitization. Herberman et al., Science 214:24 (1981). Killing of target cells occurs by inducing cell lysis. NK cells have been shown to be effective in both ex vivo therapy and in vivo treatment in patients with advanced cancer. However, endogenous NK cells (i.e., those that are harvested from a donor or from the patient) remain difficult to work with and to apply in immunotherapy. It is difficult to expand NK cells ex vivo such that they maintain their tumor-targeting, tumoricidal, and viricidal capabilities in vivo, a major obstacle to their clinical use in adoptive cell immunotherapy. Melder, et al., Cancer Research 48:3461-3469 (1988); Stephen, et al., Leuk. Lymphoma 377-399 (1992); Rosenberg, et al., New Engl. J. Med. 316:889-897 (1987). Further, preparations of endogenous NK cells include T cells and/or other immune effector cells that must be removed if the NK cells are used to treat a patient unrelated to the donor.

The NK-92 cell line is a unique cell line that was discovered to proliferate in the presence of interleukin 2 (IL-2). Gong et al., Leukemia 8:652-658 (1994). Unlike NK cells, NK-92 is a cytolytic cancer cell line which was discovered in the blood of a subject suffering from a non-Hodgkins lymphoma and then immortalized ex vivo. This cell line has high cytolytic activity against a variety of cancers. The NK-92 cell line is a homogeneous NK cell population as it relates to its lysing activity. Phase I clinical trials have confirmed its safety profile, and anti-tumor responses in certain patients with advanced cancer have been observed.

Endogenous NK cells are significantly different from NK-92 cells, in large part because of their distinct origins: NK-92 is a cancer-derived cell line, whereas endogenous NK cells are harvested from a donor (or the patient) and processed for infusion into a patient. Endogenous NK cell preparations are heterogeneous cell populations, whereas NK-92 cells are a clonal cell line that are homogenous in that they all exhibit lyzing activity. NK-92 cells readily proliferate in culture while maintaining cytotoxicity, whereas endogenous NK cells do not.

Cells, including NK cells, release a variety of components into the medium in which they are grown. Examples of such components are proteins, exosomes, and microvesicles. Exosomes are nanovesicles (up to 100 nm) that are released by a variety of normal and tumor cells. Microvesicles are similar to exosomes but larger in size (greater than 100 nm). Exosomes and microvesicles can be detected and isolated from cell culture supernatants and from body fluids (e.g., blood).

Exosomes isolated from the cell culture supernatant of endogenous NK cells contain proteins including CD56, perforin, FasL, and Rab5B. Lugini, et al. J Immunol. (2012) 189, 2833-2842. However, exosomes and other factors derived from endogenous NK cells are highly variable, both with regard to the amount of exosomes recovered and the proteins contained therein. Id. at 2839. Without being bound by theory, it is believed that this variability arises because endogenous NK cells are harvested from individual donors, and also because endogenous NK cells comprise a heterogeneous population of cells. Differences in conditions such as cell culture conditions, purification methods, initial cell populations, and the ratios of cell types in culture can all lead to variability in the composition and amount of exosomes that can be purified from endogenous NK cells. For example, certain cell populations within the NK cell preparations may be selected for or against by the purification method and/or culture conditions used.

The problems with variability that are associated with endogenous NK cells do not apply to the NK-92 cell line. Because it is a cell line, large numbers of cells can be cultured and propagated for extended periods of time. These cultures are homogeneous cell populations that provide consistent, reproducible exosome and/or microvesicle preparations. The exosomes and/or microvesicles secreted by NK-92 cells contain proteins that are contemplated to have tumoricidal properties, for example are cytotoxic and/or cytolytic. Other components may be isolated from the medium containing NK-92 cells, including components with antimicrobial properties, immunomodulatory properties, etc.

On the other hand, NK-92 cells are a cancer cell line. Some cancer cells have been shown to release exosomes containing factors that in some situations contribute to tumor growth, for example micro RNAs. Many cancer cells release exosomes and other factors that are distinct from those released by their non-malignant counterparts. For example, NK-92 cells release factors with anti-microbial properties, a characteristic not observed in endogenous NK cells. In one embodiment, the exosomes and/or microvesicles obtained from NK-92 cells are incubated in a suitable solution, such as PBS or isotonic saline, to extract such factors prior to their use. This incubation period is contemplated to significantly reduce or eliminate those factors that contribute to tumor growth.

One aspect of the invention provides pharmaceutical compositions comprising one or more components obtained from the supernatant of NK-92 cell medium. The components may be tumoricidal and/or anti-microbial. Components may also have immunomodulatory properties. These components are preferably exosomes and/or microvesicles isolated from the supernatant. In one embodiment, the exosomes and/or microvesicles are cytotoxic. In one embodiment, the exosomes and/or microvesicles have the ability to lyse cancer cells. In one embodiment, the exosomes and/or microvesicles are antimicrobial. In one embodiment, the exosomes and/or microvesicles are antiviral. In one embodiment, the exosomes and/or microvesicles are antibacterial. In one embodiment, the exosomes and/or microvesicles are immunomodulatory.

In a preferred embodiment, the pharmaceutical composition does not comprise living cells. In some embodiments, the pharmaceutical composition is an injectable composition. In some embodiments, it is contemplated that the injection will provide systemic immunomodulatory activity.

Subpopulations of NK-92 cells have been observed in culture and can be separated. Subpopulations may differ in terms of expression of cell surface markers, protein expression, etc. In one aspect of the invention, one or more subpopulations of NK-92 cells are isolated prior to obtaining the one or more components from the supernatant of NK-92 cell medium. Isolation of a defined subpopulation or subpopulations allows for consistently defined exosomes and/or microvesicles, and in particular exosomes and/or microvesicles that exhibit less or no tumoricidal properties.

In some embodiments, the pharmaceutical composition provided herein is applied to a part of the body after surgery in order to kill remaining cancer cells and/or to reduce the possibility of recurrence of the cancer. In some embodiments, the pharmaceutical composition is formulated for topical use. In some embodiments, the pharmaceutical composition is formulated to be applied subdermally. In some embodiments, the pharmaceutical composition comprises a phase-transition poloxamer.

In some embodiments, the pharmaceutical composition is an injectable form which comprises a phase transition polymer such that the composition is injected as a liquid and phase transitions to a gel in the body (e.g., at body temperature) thereby providing a drug depot.

Another aspect of the invention provides pharmaceutical compositions comprising anti-microbial (including anti-bacterial, anti-fungal and/or anti-viral) components obtained from the supernatant of NK-92 cell medium. In some embodiments, the anti-microbial components comprise tumoricidal components. In some embodiments, the anti-microbial components are exosomes and/or microvesicles isolated from the supernatant. In a preferred embodiment, the anti-microbial components comprise microvesicles isolated from the supernatant.

Another aspect of the invention provides methods of lysing cancer cells comprising administering to a human or animal patient in need thereof an antitumor or cytotoxic component isolated from the supernatant of the growth medium of NK-92 cells. In one embodiment, the component is injected into a tumor (e.g., a solid tumor). In one embodiment, the component is injected into the area around or near a tumor. In one embodiment, the component is applied topically to a tumor (e.g., skin cancer), In one embodiment, the component is administered systemically.

In some embodiments, the cancer is a carcinoma, lymphoma, sarcoma, melanoma, astrocytoma, mesothelioma cells, ovarian carcinoma, colon carcinoma, pancreatic carcinoma, esophageal carcinoma, stomach carcinoma, lung carcinoma, urinary carcinoma, bladder carcinoma, breast cancer, gastric cancer, leukemia, lung cancer, colon cancer, central nervous system cancer, ovarian cancer, cervical cancer, renal cancer, or prostate cancer. In a preferred embodiment, the cancer is skin cancer.

These and other aspects of the invention will be set forth in details below.

DETAILED DESCRIPTION OF THE INVENTION

Definitions

Before the present articles and methods are disclosed and described, it is to be understood that the aspects described below are not limited to specific compositions, preparation methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a cytokine" includes mixtures of two or more cytokines, and the like.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The term "patient" as used herein is any vertebrate organism including but not limited to mammalian patients such as humans, farm animals, domesticated pets and the like. In a preferred embodiment, the patient is a human.

The term "about" when used before a numerical value indicates that the value may vary within a reasonable range, such as ±5%, ±1%, and ±0.2%.

The term "endogenous NK cells" is used to refer to NK cells derived from a donor (or the patient), as distinguished from the NK-92 cell line. A NK cell is a cell of the immune system that kills target cells in the absence of a specific antigenic stimulus, and without restriction according to MHC class. Endogenous NK cells are generally heterogeneous populations of cells within which NK cells have been enriched. Endogenous NK cells may be intended for autologous or allogeneic treatment of a patient.

The term "NK-92 cell" includes both wild type NK-92 cells and modified NK-92 cells. NK-92 cells were found to be more cytotoxic to tumor and infected cell types than are NK cells.

The term "wild type NK-92 cell" refers to an NK cell line, NK-92, originally obtained from a patient having non-Hodgkin's lymphoma and immortalized ex vivo. NK-92 cells are available from American Type Culture Collection as Deposit No. CRL-2407, and described in, e.g., U.S. Pat. No. 7,618,817, which is incorporated by reference in its entirety.

The term "modified NK-92 cell" refers to an NK-92 cell which has been further treated to endow it with properties not found in the wild type NK-92 cell from which it is derived. Such treatments include, for example, physical treatments, chemical and/or biological treatments, and the like. The treatments confer properties upon the modified NK-92 cells that render them more advantageous for the desired purposes. Examples of modified NK-92 cells are described in, e.g., U.S. Pat. Nos. 7,618,817; 8,034,332; and 8,313,943, all of which are incorporated herein by reference in their entireties.

The term "extracellular vesicle" encompasses both exosomes and microvesicles, as well as any other vesicle secreted by a cell (e.g., a NK-92 cell) into the medium. Generally, exosomes are nanosomes that are less than about 100 nanometers (nm) in diameter. Microvesicles have a diameter of about 100 nm or larger.

As used to describe the present invention, "cancer", "tumor", and "malignancy" all relate equivalently to a hyperplasia of a tissue or organ. If the tissue is a part of the lymphatic or immune system, malignant cells may include non-solid tumors of circulating cells. Malignancies of other tissues or organs may produce solid tumors. In general, the methods of the present invention may be used in the treatment of lymphatic cells, circulating immune cells, and solid tumors.

The term "tumoricidal component" refers to components that treat cancerous tumors and/or cancer cells. Treatment of tumors encompasses reducing or eliminating the tumor, killing cancer cells, and/or inhibiting the growth, proliferation, and/or metastasis of cancer cells. Preferably, the tumor cells are killed, for example by cytolysis.

The term "anti-microbial component" refers to components that treat or prevent infection by microbes. Microbes include bacteria, fungi, molds, viruses, etc. Accordingly, anti-microbial also refers to anti-viral components, anti-bacterial components, anti-fungal components, and the like.

As used to describe the present invention, the terms "cytotoxic" and "cytolytic", when used to describe the activity of effector cells such as NK cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK cells is due to cytolysis.

The term "growth medium" or "medium" as used herein are intended to be synonymous. In general, the terms refer to any medium or aqueous solution in which the NK-92 cells may be grown or placed and into which the NK-92 cells release exosomes, microvesicles, and/or other active components. Medium may comprise growth mediums (e.g., commercially available medium) such as X-VIVO 10 or RPMI. Alternatively, medium may comprise PBS or other aqueous solution.

As used herein, "treatment," "treating," and "treat" are defined as acting upon a disease, disorder, or condition with an agent to reduce or ameliorate harmful or any other undesired effects of the disease, disorder, or condition and/or its symptoms. "Treatment," as used herein, covers the treatment of a patient, and includes: (a) reducing the risk of occurrence of the condition in a patient determined to be predisposed to the condition but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to: reducing the size or metastatic potential of a tumor; killing tumor cells; or reducing the severity of infection by an infections agent (microbe), e.g., by reducing one or more symptoms, reducing the length of time of infection, etc.

Components Isolated from the Supernatant of a Medium of NK-92 Cells

NK-92 cells can be expanded, modified and/or maintained in culture medium. Any acceptable culture conditions may be used. In one embodiment, NK-92 cells are cultured in enriched alpha minimum essential medium (MEM; Sigma Chemical Co., St. Louis, Mo.) supplemented with fetal calf serum (for example, at 12.5%; Sigma Chemical Co., St. Louis, Mo.), and/or horse serum (for example, at 12.5%; Sigma Chemical Co., St. Louis, Mo.). In another embodiment, the NK-92 cells are cultured in XVivo 10 medium supplemented with human serum, human plasma, or human serum albumin (for example, at 5%). In a preferred embodiment, the serum, plasma, or serum albumin is exosome-depleted prior to culture of the NK-92 cells.

The medium optionally is supplemented with other nutrients, cytokines, and/or growth factors, for example interleukin 2 (IL-2), L-asparagine, L-glutamine, and/or L-serine. NK-92 cells, when in the medium, can release components such as proteins (e.g., cytokines), microvesicles, and/or exosomes to the medium. After the cells are isolated from the medium, for example, by centrifugation, the components released from the cells remain in the supernatant.

Another suitable medium employed includes X-VIVO 10 medium, 5% human serum AB, 36 µM L-asparagine, 450 µM L-glutamine, 324 µM L-serine, and 500 IU of IL-2.

In some embodiments, the medium is serum-free medium, PBS, or other aqueous solution, for example Ringer's solution, dextrose solution, Hank's solution, and other aqueous physiologically balanced salt solutions. Without being bound by theory, some components of growth medium (e.g., serum) may contain exosomes, microvesicles, and/or other components that are unrelated to NK-92 cells. Accordingly, it may be beneficial to maintain the NK-92 cells in serum-free medium or other aqueous solution for a period of time before isolating exosomes, microvesicles, or other components from the medium. Alternatively, the NK-92 cells may be cultured in exosome-depleted or exosome-free serum or serum alternative.

In some embodiments, one or more stimulatory agents are added to the medium. Without being bound by theory, it is believed that stimulation of NK-92 cells with such agents may result in more consistent, robust, and/or reproducible release of components, including exosomes and/or microvesicles. Stimulatory agents include, for example, cytokines or pharmaceutical stimulators. In one embodiment, the stimulatory agent is IL-15. In one embodiment, the stimulatory agent is interferon gamma.

In some embodiments, the one or more tumoricidal and/or antimicrobial components comprise exosomes isolated from the supernatant. In some embodiments, the one or more tumoricidal and/or antimicrobial components comprise microvesicles isolated from the supernatant. In some embodiments, the one or more tumoricidal and/or antimicrobial components comprise exosomes and microvesicles isolated from the supernatant.

Exosomes are nanovesicles excreted from the cells, having a diameter up to about 100 nm. In some embodiments, they have a diameter of about 30 to about 100 nm. Microvesicles are non-cellular and have a diameter of greater than about 100 nm and preferably are less than about 1.5 microns.

Exosomes and/or microvesicles can be isolated from medium by a number of methods. One method is by ultracentrifugation. Other methods include commercially available exosome isolation kits (e.g., Total Exosomes Isolation kit [Life Technologies], Exo-spin™ Exosome Purification Kit [Cell Guidance Systems], or PureExo® Exosome Isolation Kit [101 Bio]); commercially available instruments, such as Dynabeads® Human CD63-specific purification system or Dynabeads® Streptavidin purification system (available from Life Technologies Corporation); filtration; or differential centrifugation methods (e.g., those described in S. Rani et al., *Methods Mol Biol.*, 784:181-95 (2011)). The presence, size, and purity, etc. of exosomes and/or microvesiclescan be characterized by methods, such as Western blotting, transmission electron microscopy, flow cytometry, atomic force microscopy, nanoparticle tracking analysis, Raman microspectroscopy, resistive pulse sensing, and transmission electron microscopy.

In some embodiments, the NK-92 cells comprise wild type NK-92 cells.

In some embodiments, the NK-92 cells comprise modified NK-92 cells. NK-92 cells can be modified by methods known in the art, such as those described in U.S. Pat. No. 7,618,817, which is incorporated herein by reference in its entirety. For example, the NK-92 cells can be modified to express a Fc receptor on a surface of the cell. The Fc receptor can be an activating Fcγ receptor, CD16 (FcγRIII-A), FcγRI (CD64), FCγRII (CD32), FCγRIII, FcRn, Fcα and FCε, etc. The Fc receptors can be of any binding affinity for their ligands, or fragments of their ligands, including low- and high-binding affinity forms. The NK-92 cells can be further modified to express one or more associated accessory signaling polypeptides, such as FcεRI-γ or TCR-ζ, cytokines, or fragments thereof.

In some embodiments, the NK-92 cells comprise NK-92 cells modified to express Fc receptors. In some embodiments, the NK-92 cells comprise NK-92 cells modified to express FcγRIII-A, FCγRI, FCγRII, FCγRIII, FcRn, Fcα or FCε, or a combination thereof. In some embodiments, the NK-92 cells comprise NK-92 cells modified to express one or more chimeric antigen receptors. In some embodiments, the NK-92 cells comprise modified NK-92 cells available from American Type Culture Collection as Deposit No. PTA-8836, PTA-6967, PTA-8837 or PTA-6672, or a combination thereof. In some embodiments, the NK-92 cells comprise NK-92-CD16, NK-92-CD16-γ, or NK-92-CD16-ζ, or a combination thereof.

In some embodiments, the NK-92 cells comprise NK-92 cells modified to express a cytokine. In some embodiments, the NK-92 cells comprise NK-92 cells modified to express a cytokine that promotes growth of the cells and/or a cytokine receptor. In some embodiments, the NK-92 cells comprise NK-92 cells modified to express IL-2 and/or IL-2 receptor. In some embodiments, the NK-92 cells comprise NK-92 cells modified to express IL-15, IL-18, or IL-21, or a receptor thereof. In some embodiments, the NK-92 cells comprise modified NK-92 cells available from American Type Culture Collection as Deposit No. CRL-2408 or CRL-2409, or a combination thereof. In some embodiments, the NK-92 cells comprise NK-92MI, NK-92CI, or a combination thereof.

Without being bound by theory, it is believed that exosomes and/or microvesicles from modified NK-92 cells will be distinct from those from wild type NK-92 cells. For example, exosomes and/or microvesicles from modified NK-92 cells may contain different receptors and/or other proteins (e.g., cytolytic enzymes), based on the modification(s) of the cells. Exosomes and/or microvesicles from modified NK-92 cells may also contain different amounts or relative amounts of some receptors and/or other proteins.

Pharmaceutical Compositions

In one aspect, provided is a pharmaceutical composition useful for killing cancer cells in a warm-blooded animal, which composition comprises a pharmaceutically acceptable carrier and one or more components isolated from the supernatant of a growth medium of NK-92 cells.

In some embodiments, the pharmaceutical composition is liquid at room temperature and a gel when applied to the patient. In some embodiments, the pharmaceutically acceptable carrier comprises a poloxamer.

In another aspect, provided is a pharmaceutical composition comprising exosomes and/or microvesicles isolated from the supernatant of a growth medium of NK-92 cells and a sterile aqueous carrier.

In another aspect, provided is a kit comprising a first pharmaceutical composition comprising a pharmaceutically acceptable carrier and exosomes and/or microvesicles isolated from the supernatant of a growth medium of NK-92 cells, and a second pharmaceutical composition comprising a gel, wherein the first pharmaceutical composition and the second pharmaceutical composition are topical formulations. In some embodiments, the second pharmaceutical composition a poloxamer. In some embodiments, the second pharmaceutical composition comprises exosomes and/or microvesicles isolated from the supernatant of a growth medium of NK-92 cells. In a preferred embodiment, the first and/or second pharmaceutical component comprises microvesicles.

In some embodiments, the first pharmaceutical composition comprises a liquid and the second pharmaceutical composition comprises a gel, poloxamer, or composition that is a liquid at room temperature and a gel at body temperature. The liquid is applied to the treatment area first, and the gel is applied over the liquid. Without being bound by theory, it is believed that the liquid formulation provides rapid treatment of the area, while the gel maintains the liquid at the site of application. In some embodiments, the gel comprises exosomes and/or microvesicles isolated from the supernatant of a growth medium of NK-92 cells and a sterile aqueous carrier. Without being bound by theory, it is believed that the gel will provide slower release of exosomes and/or microvesicles to the treatment area, thus providing for sustained release and treatment of the affected area.

In some embodiments, the pharmaceutical composition further comprises one or more cytokines.

The tumoricidal and/or antimicrobial component(s) may be administered in conjunction with a cytokine such as IFN-γ, TGF-β, IL-4, IL-10, IL-13, IL-2, etc., in order to maintain the functional effectiveness of the composition comprising the tumoricidal and/or antimicrobial component(s). The term "in conjunction" indicates that the cytokine may be administered shortly prior to administration of the composition comprising the component, or it may be given simultaneously with the composition comprising the component, or shortly after the composition comprising the tumoricidal component has been administered. The cytokine may also be given at two such times, or at all three times with respect to the time of administering the composition comprising the tumoricidal component. In some embodiments, the cytokine and the component are administered in a single composition.

In some embodiments, the one or more cytokines includes at least IL-2.

The pharmaceutical composition can be in a variety of formulations suitable for oral, topical, transdermal, rectal, inhalation, or parenteral (intravenous, intramuscular, or intraperitoneal) administration, and the like. The pharmaceutical composition can be in a formulation suitable for injection into a tumor or at or around a tumor site. In one embodiment, the pharmaceutical composition is injected or applied to a tumor site after surgery to remove all or most of the tumor.

As used herein "pharmaceutically acceptable carrier" or "pharmaceutically acceptable excipient" includes any and all solvents, dispersive agents or media, coating(s), antimicrobial agents, iso/hypo/hypertonic agents, absorption-modifying agents, and the like, suitable for pharmaceutical use and compatible with the tumoricidal and/or antimicrobial components. Moreover, other or supplementary active ingredients can also be incorporated into the final composition.

The pharmaceutical compositions described herein can be administered in a number of ways depending on whether local or systemic treatment is desired, and on the area to be treated. In one aspect, administration can be by injection, where the composition is formulated into a liquid or gel. In other aspects, the composition can be formulated to be applied internally to a patient. In other aspects, the composition can be applied topically (including ophthalmically, vaginally, rectally, intranasally, orally, or directly to the skin) For example, a topical composition comprising exosomes and/or microvesicles can be applied to any accessible tumor or infection, e.g. a skin tumor or other tumor (e.g., Kaposi's sarcoma); a viral infection (e.g., warts, genital warts, herpes); or a bacterial infection.

In some embodiments, the pharmaceutical composition is an injectable formulation.

The pharmaceutical composition may be administered parenterally, e.g., intravenously, intramuscularly, intravenously, subcutaneously, or interperitonically. The composition can be injected systemically or locally to or near the site of a cancer. A single intravenous or intraperitoneal dose can be administered. Alternatively, a slow long-term infusion or multiple short-term daily infusions may be utilized, typically lasting from 1 to 8 days. Alternate day or dosing once every several days may also be utilized.

Sterile, injectable compositions are prepared by incorporating the tumoricidal and/or antimicrobial components in a suitable amount into an appropriate carrier. Suitable carriers include aqueous carriers, such as water and aqueous buffer (e.g., phosphate buffered saline (PBS), citrate buffer, etc.), water-soluble organic solvents (e.g., polyethylene glycol 300, polyethylene glycol 400, ethanol, propylene glycol, glycerin, N-methyl-2-pyrrolidone, dimethylacetamide, and dimethylsulfoxide), organic liquids/semi-solids (beeswax, d-tocopherol, oleic acid, medium-chain mono- and diglycerides), non-ionic surfactants (polyethoxylated castor oils (e.g., Cremophor EL, Cremophor RH 40, Cremophor RH 60), polysorbate 20, polysorbate 80, poloxamer 188, poloxamer 407, d-tocopherol polyethylene glycol 1000 succinate, polyethylene glycol (15)-hydroxystearate, sorbitan monooleate, oleoyl polyoxyl-6 glycerides, linoleoyl polyoxyl-6 glycerides, caprylocaproyl polyoxyl-8 glycerides, Gellucire® 44/14, Softigen® 767, and mono- and di-fatty acid esters of PEG 300, 400, or 1750, etc.), a lipid (e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil), cyclodextrin (such as α-cyclodextrin, β-cyclodextrin, and γ-cyclodextrin, hydroxypropyl-β-cyclodextrin, and sulfobutylether-β-cyclodextrin), and phospholipids (e.g., phosphatidylcholine, phosphatidylethanolamine, phosphatidylserine, distearoylphosphatidylglycerol, 1-dimyristoylphosphatidylcholine, 1-dimyristoylphosphatidylglycerol, etc.), or a mixture thereof. In some embodiments, the aqueous carrier comprises hyaluronic acid, saline, Ringer's solution, dextrose solution, Hank's solution, and other aqueous physiologically balanced salt solutions. In some embodiments, the nonaqueous carrier comprises fixed oils, vegetable oils such as olive oil and sesame oil, triglycerides, propylene glycol, polyethylene glycol, or injectable organic esters such as ethyl oleate. In some embodiments, the pharmaceutically acceptable carrier further comprises a viscosity enhancing agent, such as carboxymethylcellulose or salts thereof, sorbitol, or dextran; a substance that enhance isotonicity and chemical stability, such as phosphate buffer, bicarbonate buffer and Tris buffer; a preservative such as thimerosal, cresols, formalin and benzyl alcohol.

The injectable compositions can be in a solution or suspension, but should be able to pass readily through an injection device such as a hollow needle. A proper viscosity may be achieved and maintained by the proper choice of solvents or excipients. In some embodiments, the pharmaceutical acceptable carrier comprises a viscosity enhancing agents. In some embodiments, the composition has a viscosity of between about 5 centipoise (cP) to about $1 \times 10^6$ cP, or about 5 cP to about $1 \times 10^5$ cP, or about 5 cP to about $1 \times 10^4$ cP, or about 5 cP to about $1 \times 10^3$ cP, or about 6 cP to about 100 cP at 25° C.

In some embodiments, the pharmaceutical composition is an injectable extended release formulation. The tumoricidal and/or antimicrobial components in the extended release formulation can be released from the composition to the body over an extended period of time, such as over at least several minutes, at least one hour, at least several hours, at least one day, at least several days, or in weeks, etc. to provide long term and/or continuous therapeutic effect.

In some embodiments, the composition comprises a localization agent which allows for localized retention of the composition when delivered to or proximate to site of a tumor, optionally for extended and/or continuous release of the tumoricidal and/or antimicrobial component in the composition. Such agents include thixotropic agents, phase changing agents, such as hydrogel, bioerodible, biocompatible polymer, and collagen gels, and the like. These compositions are in an injectable or liquid form at ambient conditions and form a viscous or gel-like bioerodible or biodegradable mass after application which limits transport away from the site of delivery and allows for the diffusion of the tumoricidal and/or antimicrobial component from the composition.

The hydrogels useful in the compositions can be chemically and/or physically cross-linked hydrogels. In situ chemical cross-linking is obtained, e.g., via photo-initiated, redox-initiated or Michael-type addition polymerization that preferably involve covalent bond formation. Physically cross-linked hydrogels self-assemble under external stimuli and do not rely on covalent bond formation. Temperature, pH, ion concentration, and hydrophobic interactions are certain of the external stimuli useful for such self-assembly and for the immobilization of such hydrogels.

Exemplary polymers suitable for the use in the compositions include polylactides, polyglycolides, poly(caprolactone), polyanhydrides, polyamines, polyesteramides, polyorthoesters, polydioxanones, polyacetals, polyketals, polycarbonates, polyphosphoesters, polyorthocarbonates, polyphosphazenes, succinates, poly(malic acid), poly(amino acids), polyvinylpyrrolidone, polyethylene glycol, polyhydroxycellulose, polyphosphoesters, polysaccharides, chitin, chitosan, hyaluronic acid, and copolymers, such as poloxamers, terpolymers and mixtures thereof.

In some embodiments, the localization agent is a poloxamer. Poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, poloxamer has the formula $$HO(C_2H_4O)_b(C_3H_6O)_a(C_2H_4O)_bOH$$

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the trade name Pluronic® manufactured by BASF. Non-limiting examples of poloxamers useful herein include, but are not limited to, Pluronic® F68, P103, P105, P123, F127, and L121. At suitable concentrations, such as 10%-30% w/w of poloxamer, a poloxamer solution is a liquid at room temperature and forms a soft gel in the body.

Suitable collagens include, for example, alkaline treatment of insoluble collagen extracted from various animals, or by treating with enzyme such as pepsin, trypsin, chymotrypsin, papin or pronase. Collagen can be obtained from the skin, bone, cartilage, tendon or organs, etc. of birds or mammals. Collagen can be flexible after curing and requires only a short time for crosslinking, in other words, requires only a short time for gelation. Collagen solution can also be made by dissolving collagen in a non-toxic solvent, examples of which include water, physiological saline, a buffer such as borate buffer, or an aqueous solution containing a salt such as sodium chloride, sodium bromide and potassium bromide, or protein, sugar or lipid, etc.

The collagen can also form a gel even in the presence of moisture such as that in blood or tumor, and can demonstrate a high degree of adhesiveness with respect to living body tissue. Collagen solutions used in the present invention can be made at various concentrations, neutralized and prepared for injection. In various embodiments, the concentration of collagen in the composition can be at 0.2 mg/mL, 0.5 mg/mL, 0.75 mg/mL, 1 mg/mL, 2 mg/mL, 3 mg/mL, 4 mg/mL, 5 mg/mL, 6 mg/mL, 7 mg/mL, 8 mg/mL, 10 mg/mL, 20 mg/mL, 30 mg/mL, 40 mg/mL and 50 mg/mL, or any range between two of the numbers. Upon injection into an organ, chilled collagen gels can thermogel as they reach body temperature or about 37° C.

In some embodiments, the pharmaceutical composition provides extended, sustained, and/or continuous release of the tumoricidal and/or antimicrobial component(s) of the composition.

Sterilization of the composition can be done by known procedures, such as filtration.

The final form should be stable under conditions of manufacture and storage. Furthermore, the final pharmaceutical form should be protected against contamination and should, therefore, be able to inhibit the growth of microorganisms such as bacteria or fungi.

Prevention or inhibition of growth of microorganisms may be achieved through the addition of one or more antimicrobial agents such as chlorobutanol, ascorbic acid, parabens, thimerosal, or the like. It may also be preferable to include agents that alter the tonicity such as sugars or salts.

The pharmaceutical composition can also be made as a sterile powder. Sterile powder comprising the tumoricidal and/or antimicrobial components can be prepared by methods including vacuum drying or freeze drying of a liquid composition, such as a composition comprising an aqueous carrier. The sterile powder can be reconstituted with a suitable amount of an aqueous carrier, such as PBS, to provide an injectable composition for administration to a patient.

In some embodiments, the compositions are formulated as a topical composition applied directly to the skin for treating a skin cancer. In some embodiments, the compositions are formulated as a topical composition applied directly to other accessible cancers, for example cervical cancer or oral cancers. In some embodiments, the topical composition is applied to virus-infected cells, for example a wart. In some embodiments, the wart is a genital (venereal) wart. In some embodiments, the wart is a common wart, flat wart, filiform/digitate wart, mosaic wart, periungal wart, or plantar wart.

Formulations for topical administration can include, emulsions, creams, aqueous solutions, oils, ointments, pastes, gels, lotions, milks, foams, suspensions and powders. In some embodiments, the pharmaceutical composition is a cream or lotion. In one aspect, the topical composition can include one or more surfactants and/or emulsifiers. In one embodiment, the emulsifier does not alter the structure of the exosomes and/or microvesicles. In one embodiment, the emulsifier alters the structure of the exosomes and/or microvesicles. For example, the emulsifier may destroy the exosome and/or microvesicle structure, thereby releasing active factors within the exosomes and/or microvesicles.

Surfactants (or surface-active substances) that may be present are anionic, non-ionic, cationic and/or amphoteric surfactants. Typical examples of anionic surfactants include, but are not limited to, soaps, alkylbenzenesulfonates, alkanesulfonates, olefin sulfonates, alkyl ether sulfonates, glycerol ether sulfonates, α-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. Examples of non-ionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. Examples of amphoteric or zwitterionic surfactants include, but are not limited to, alkylbetaines, alkylamidobetaines, aminopropionates, aminoglycinates, imidazolinium-betaines and sulfobetaines.

In some embodiments, the surfactant can be fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, alpha-olefinsulfonates, ether carboxylic acids, alkyl oligoglucosides, fatty acid glucamides, alkylamidobetaines, amphoacetals and/or protein fatty acid condensates.

Examples of zwitterionic surfactants include betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate.

In some embodiments, the emulsifier can be a nonionogenic surfactant selected from the following: the addition products of from 2 to 30 mole of ethylene oxide and/or 0 to 5 mole of propylene oxide onto linear fatty alcohols having 8 to 22 carbon atoms, onto fatty acids having 12 to 22 carbon atoms, onto alkylphenols having 8 to 15 carbon atoms in the alkyl group, or onto alkylamines having 8 to 22 carbon atoms in the alkyl radical; alkyl and/or alkenyl oligoglycosides having 8 to 22 carbon atoms in the alk(en)yl radical and the ethoxylated analogs thereof; the addition products of from 1 to 15 mole of ethylene oxide onto castor oil and/or hydrogenated castor oil; the addition products of from 15 to 60 mole of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mole of ethylene oxide; partial esters of polyglycerol (average degree of self-condensation 2 to 8), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mole of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; and block copolymers, e.g. polyethylene glycol-30 dipolyhydroxystearates.

In some embodiments, the emulsifier is a polyalkylene glycol such as, for example, polyethylene glycol or polypropylene glycol. In some embodiments, the emulsifier is polyethylene glycol having a molecular weight 100 Da to 5,000 Da, 200 Da to 2,500 Da, 300 Da to 1,000 Da, 400 Da to 750 Da, 550 Da to 650 Da, or about 600 Da.

In some embodiments, the emulsifier is a poloxamer as described herein.

In some embodiments, the emulsifier is composed of one or more fatty alcohols. In some embodiments, the fatty alcohol is a linear or branched $C_6$ to $C_{35}$ fatty alcohol. Examples of fatty alcohols include, but are not limited to, capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z,12Z-octadecadien-1-ol), elaidolinoleyl alcohol (9E,12E-octadecadien-1-ol), linolenyl alcohol (9Z,12Z,15Z-octadecatrien-1-ol) elaidolinolenyl alcohol (9E,12E,15-E-octadecatrien-1-ol), ricinoleyl alcohol (12-hydroxy-9-octadecen-1-ol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol), geddyl alcohol (1-tetratriacontanol), or cetearyl alcohol.

In some embodiments, the carrier used to produce the topical composition is a mixture of polyethylene and one or more fatty alcohols. For example, the carrier comprises about 50% to about 99% by weight, about 75% to about 99% by weight, about 90% to about 99% by weight, or about 95% by weight polyethylene glycol and about 1% to about 50% by weight, about 1% to about 25% by weight, about 1% to about 10% by weight, or about 5% by weight fatty alcohol. In some embodiments, the carrier is a mixture of polyethylene glycol and cetyl alcohol.

The topical compositions can also include additional components suitable in such compositions. In some embodiments, the topical composition can include one or more of the following components: fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, swelling agents, insect repellents, hydrotropes, solubilizers, preservatives, perfume oils and dyes. Examples of each of these components are disclosed in U.S. Pat. No. 8,067,044, which is incorporated by reference with respect these components.

The topical compositions comprising the tumoricidal and/or antimicrobial component(s) described herein can be prepared by mixing the component(s) with the carrier for a sufficient time such that the particles are evenly dispersed throughout the carrier. In the case when the carrier comprises two or more components, the components can be admixed with one another prior to the addition of the tumoricidal and/or antimicrobial component. The amount of tumoricidal and/or antimicrobial components present in the topical composition can vary depending upon the application. In some embodiments, the tumoricidal and/or antimicrobial component is from 0.5% to 20%, 1% to 10%, 2% to 5%, or about 3% by weight of the topical composition.

It will be appreciated that the amounts of the tumoricidal and/or antimicrobial components in the composition in a specified case will vary according to the specific tumoricidal and/or antimicrobial components being utilized, the particular compositions formulated, the mode of application, and the particular situs and patient being treated. Dosages for a given host can be determined using conventional considerations, e.g. by customary comparison of the differential activities of the composition and of a known therapy, e.g., by means of an appropriate conventional pharmacological protocol. Physicians and formulators, skilled in the art of determining doses of pharmaceutical agents, will have no problems determining dose according to standard recommendations (Physician's Desk Reference, Barnhart Publishing (1999)).

Unit doses or multiple dose forms are contemplated, each offering advantages in certain clinical settings. The unit dose would contain a predetermined quantity of the tumoricidal and/or antimicrobial components calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular tumoricidal and/or antimicrobial component, the particular therapeutic effect to be achieved, the disease to be treated, and the conditions of the patient, etc.

A unit dose will contain a therapeutically effective amount sufficient to treat a disease in a patient and may contain from about 0.001 mg to 100 mg of the tumoricidal, cytotoxic, and/or antimicrobial component. The amount of the tumoricidal, cytotoxic and/or antimicrobial component can vary from 0.001% to 90% w/w of the composition, such as 0.001%, 0.01%, 0.1%, 1%, 10%, 50%, or 90%, or in any range between any two numbers. The disease treated may be any disease treatable by the exosomes of the invention, for example a cancer, a bacterial infection, a viral infection, or a fungal infection.

The pharmaceutical composition can further be in an oral formulation such as an ingestible tablet, a buccal tablet, capsule, caplet, elixir, suspension, syrup, trouche, wafer, lozenge, and the like.

The composition may be a sustained-release preparation. The composition may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained.

The suitable formulation of an oral composition may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such as peppermint, oil of wintergreen or the like. Various other material may be present as coating or to otherwise modify the physical form of the oral dosage unit. The oral dosage unit may be coated with shellac, a sugar or both. Syrup or elixir may contain the tumoricidal and/or antimicrobial components, sucrose as a sweetening agent, methyl and propylparabens as a preservative, a dye and flavoring. Any material utilized should be pharmaceutically-acceptable and substantially non-toxic.

Additional descriptions of preparing a pharmaceutical composition can be found in the $19^{th}$ Edition of Remington's Pharmaceutical Sciences, Published by the Mack Publishing Co., Easton, Pa. 18040. The pertinent portions are incorporated herein by reference.

Method of Treatment of the Invention

The compositions described herein are useful in treating a variety of diseases, such as cancer. Examples of diseases that can be treated by the compositions include malignancies of the immune system, the lymphatic system, and the hematopoietic system, formed tumors, and solid tumors. Non-limiting examples of cancers that can be treated with the compositions include mast cell leukemia, acute myelogenous leukemia (AML), erythroleukemia, myeloid disorders (e.g., myeloid leukemia, multiple myeloma, and erythroleukemia), germ cell tumors, lung carcinoma, small-cell lung carcinoma, gastrointestinal stromal tumors, neuroblastoma, cervical carcinoma, ovarian carcinoma, brain carcinoma, breast carcinoma, ovary carcinoma, endometrium carcinoma, kidney carcinoma, thyroid carcinoma, bladder carcinoma, colon carcinoma, pancreas carcinoma and prostate carcinoma, skin carcinoma such as melanoma, adenomas (e.g., villous colon adenoma), and sarcomas (e.g., osteosarcoma), etc.

In some embodiments, the pharmaceutical compositions described herein are used to treat skin cancer, for example melanoma, squamous cell cancer, basal cell cancer, or mast cell tumors.

In some embodiments, the pharmaceutical compositions described herein are used to treat other epithelial cell cancers, for example cervical cancer or oral cancer. In some embodiments, the pharmaceutical compositions described herein are used to treat virus-infected cells, for example warts.

In some embodiments, the pharmaceutical compositions described herein are used to modulate the immune system. For example, exosomes and/or microvesicles may induce cytotoxic T cell response (e.g., against tumors), and/or induce apoptosis (e.g., of activated immune cells). Exosomes and/or microvesicles may also play a role in immune surveillance.

In some embodiments, the pharmaceutical compositions described herein are useful in treating infections. In one embodiment, the pharmaceutical compositions described herein are useful in treating infections by pathogenic viruses. Pathogenic viruses include, without limitation, human papillomavirus, human immunodeficiency virus, Epstein-Barr virus, cytomegalovirus, Ebola virus, Marburg virus, influenza, respiratory syncytial virus, poxvirus, varicella-zoster virus, and herpes. In one embodiment, the pharmaceutical compositions described herein are useful in treating bacterial infections. Infectious bacteria include, without limitation, *streptococcus*, *staphylococcus*, *Cryptococcus*, *Chlamydia*, *Escherichia*, *Pseudomonas*, *Clostridium*, and *Candida*, including antibiotic-resistant strains of any of the above. In one embodiment, the pharmaceutical compositions described herein are useful in treating infections caused by other microbes, including fungus and yeast.

With mammals, including humans and domesticated animals, the effective amount can be administered on the basis of body surface area to be covered (e.g., affected area), for example in a topical composition. A suitable dose range is from about 0.001 mg to about 100 mg of equivalent per $m^2$ body surface area of a tumoricidal and/or antimicrobial component, for instance from about 0.005 $mg/m^2$ to about 50 $mg/m^2$. The dosage can be administered daily, such as once, twice, three times or more per day, or every two or several days, or every week, etc. The frequency of administration can be reduced if an extended release formulation is administered.

In one embodiment, the effective amount can be administered on the basis of tumor volume. A suitable dose range is from about 1:100 to about 1:10,000 exosome/microvesicle preparation to tumor volume ratio. In one embodiment, the suitable dose range from about 1:100 to about 1:1,000 exosome/microvesicle preparation to tumor volume ratio. In one embodiment, the suitable dose range from about 1:1,000 to about 1:10,000 exosome/microvesicle preparation to tumor volume ratio.

In one embodiment, the effective amount can be administered based on patient body weight. A suitable dose range is from about 1 µg to about 100 mg exosome/microvesicle preparation per kg body weight. In one embodiment, the suitable dose range from about 1 µg to about 10 mg exosome/microvesicle preparation per kg body weight. In one embodiment, the suitable dose range from about 1 µg to about 100 µg exosome/microvesicle preparation per kg body weight. In one embodiment, the suitable dose range from about 10 µg to about 10 mg exosome/microvesicle preparation per kg body weight. In one embodiment, the suitable dose range from about 100 µg to about 10 mg exosome/microvesicle preparation per kg body weight.

The dosage and frequency of administration may depend on the type of formulation, the disease being treated, the amount of the tumoricidal and/or antimicrobial component, the patient's age, gender, species, other conditions, etc.

Combination Therapy

In another aspect, the compositions described herein can be administered in conjunction with other cancer therapies, such as surgery, radiation, chemotherapy (e.g., cisplatin, carboplatin, oxaliplatin, satraplatin, and picoplatin, especially cisplatin and carboplatin; taxanes, such as paclitaxel and docetaxel; and anthracyclines such as daunorubicin, doxorubicin, epirubicin, idarubicin, or valrubicin, etc.), cell based therapy (e.g., NK-92 cell therapy), antibody therapy, etc. In some embodiments, the composition can be administered in conjunction with one or more cytokines as described herein.

The following examples are included to illustrate the invention and not to limit the invention. All publications or references cited in the present specification are hereby incorporated by reference.

EXAMPLES

Example 1

Antimicrobial Effect of NK-92 Cells

NK-92 cells were incubated with *Cryptococcus neoformans* in round-bottom plates in Myelocult medium for 24 hours. An effector:target (NK-92: *C. neoformans*) ratio of 100:1 ($1 \times 10^6$:$1 \times 10^4$ cells/well) was used. *C. neoformans* ($1 \times 10^4$ cells/well) were incubated in Myelocult medium without NK-92 cells as a control. After the 24 hour incubation, the cultures were serially diluted and plated on Sabouraud agar plates. Plates were incubated at room temperature for 48 hours. The number of colonies at each dilution were measured.

Figure 1:
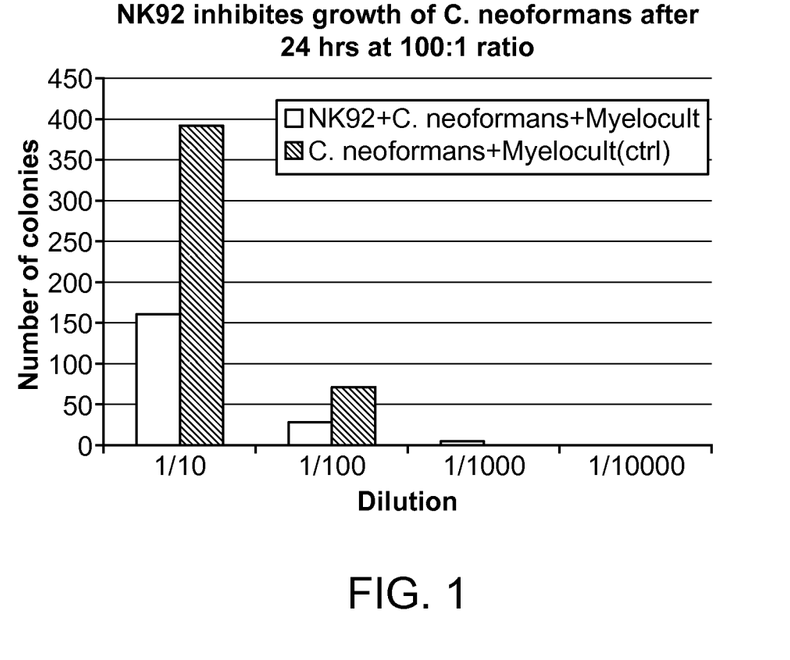
FIG. 1 shows the effect of NK-92 cells on *Cryptococcus neoformans* growth.
Figure 2:
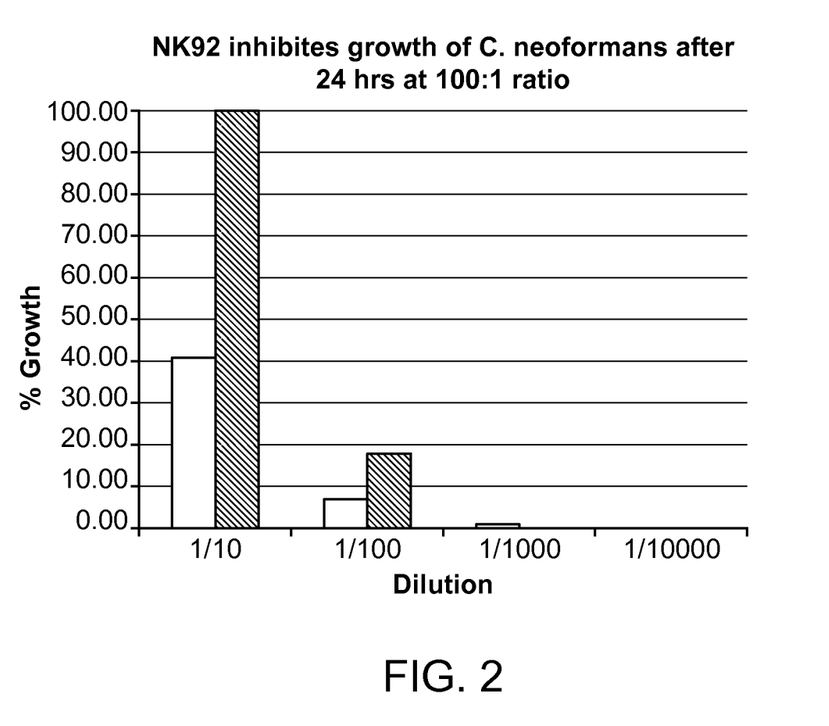
FIG. 2 shows the same data as in FIG. 1, expressed as a percent of *C. neoformans* growth.

The number of colonies per plate at each dilution are indicated in FIG. 1. White bars: NK-92 cells+*C. neoformans*. Black bars: *C. neoformans* alone. FIG. 2 indicates that NK-92 cells inhibited *C. neoformans* growth by approximately 60%.

Similar results were observed when NK-92 cells were incubated with another species of fungus (a species of *Aspergillus*). NK-92 cells caused hyphal damage to the fungus in a dose- and time-dependent manner.

Example 2

Isolation of Exosomes and/or Microvesicles from NK-92 Cell Supernatant

Extracellular vesicles (exosomes and/or microvesicles) were isolated by ultracentrifugation. Cultured NK-92 cells were centrifuged at 300×g for 10 minutes, and the cell pellet discarded. The supernatant was centrifuged at 2000×g for 20 minutes, and the pellet (cell debris) was discarded. The resulting supernatant was subjected to ultracentrifugation at 100,000×g for 80 minutes. The resulting pellet was washed with phosphate-buffered saline and subjected to ultracentrifugation at 100,000×g for 80 minutes. The washed pellet containing exosomes and microvesicles (EV/MV preparation) was retained for further studies.

Example 3

Characterization of Extracellular Vesicles

NK-92 cells were cultured under a variety of conditions, and the extracellular vesicles were isolated from the media as described in Example 2. The culture conditions are provided in Table 1. Cells were conditioned in exofree FBS for at least 24 to 46 hours prior to harvesting of exosomes. ExoFree FBS is exosome depleted to avoid contamination of the NK-92 extracellular vesicle preparations.

TABLE 1

NK-92 Growth Conditions

| Lane | Number of cells | Media Backbone | ExoFree FBS (%) | IL-2 (IU/mL) |
|---|---|---|---|---|
| 4 | $4.0 \times 10^7$ | αMEM(NK) | 5 | 500 |
| 5 | $4.8 \times 10^7$ | RPMI | 10 | 500 |
| 6 | $4.0 \times 10^7$ | X-Vivo10[1] | 5 | 500 |
| 7 | $3.6 \times 10^7$ | X-Vivo10[1] | 0 | 500 |

[1]Lonza Group Ltd.

Figure 3A:
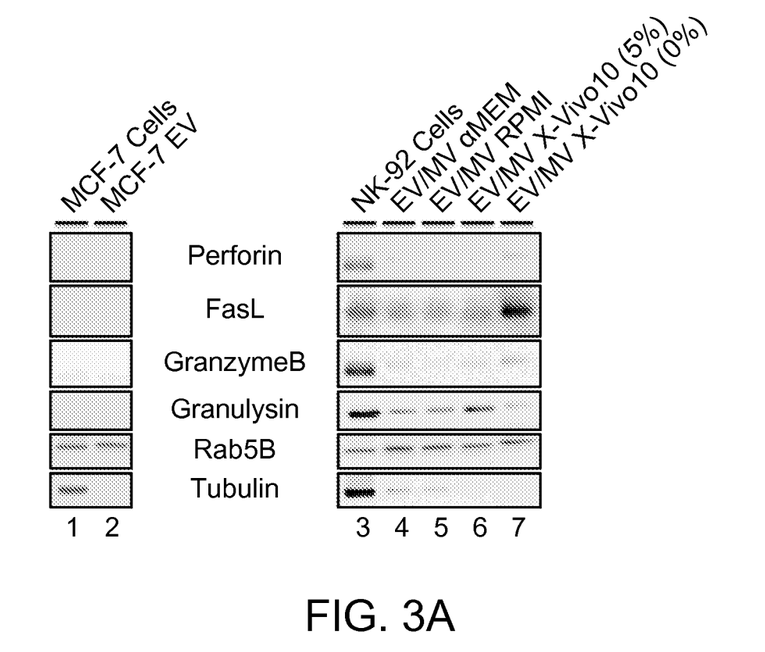
FIG. 3A is a picture of a Western blot analyzing the protein content of exosomes/microvesicles (EV/MV) isolated from NK-92 cells under a variety of culture conditions (lanes 4-7). NK-92 cells (lane 3) are used as a positive control. MCF-7 cells (lane 1) and exosomes (EV, lane 2) are positive controls for tubulin and/or Rab5B, and negative controls for cytolytic proteins.
Figure 3B:
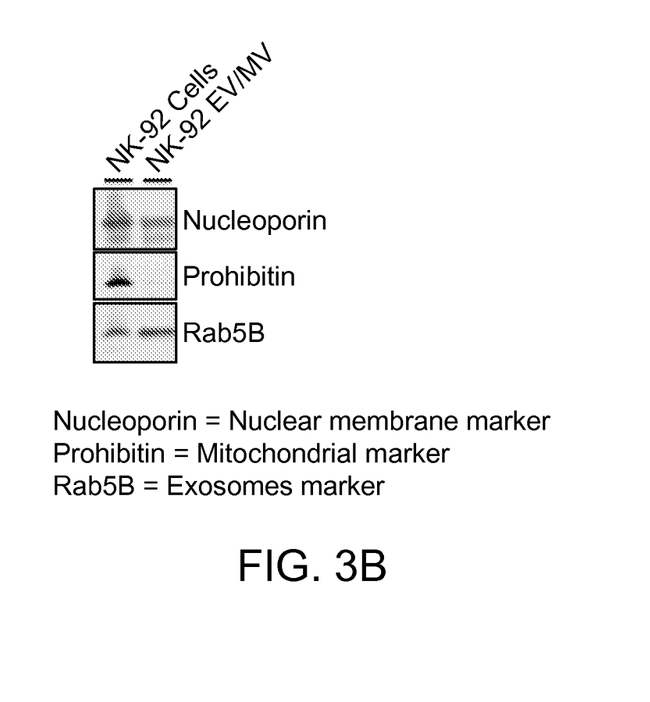
FIG. 3B is a picture of a Western blot analyzing the presence of markers for nuclear membrane (nucleoporin), mitochondria (prohibitin) and exosomes (Rab5B) in NK-92 cells and exosome/microvesicle preparation.

EV/MV preparations were analyzed for the presence of several proteins using standard Western blotting techniques, as shown in FIG. 3A and FIG. 3B. The MCF-7 cell line was used as a positive control for exosome production and a negative control for cytolytic proteins. NK-92 cell pellet (NK-92 cells) were used as a positive control. MCF-7 cells were cultured in DMEM with 10% ExoFree fetal bovine serum (FBS) and 2 mM L-Glutamine.

Extracellular vesicles from both NK-92 and MCF-7 cells were positive for Rab5B, an exosome marker. NK-92 EV/MV preparations (but not MCF-7 EV/MV preparations) were also positive for several apoptosis-inducing and/or cytolytic proteins that are known to be involved in NK cell activity, including perforin, Fas ligand (FasL), granzyme B, and granulysin. However, the amount of each of these proteins appears to be dependant on NK-92 cell growth conditions, including media backbone (e.g., αMEM(NK), RPMI, X-Vivo) and serum concentration.

EV/MV preparations from NK-92 cells were analyzed for contamination by other organelles. EV/MV isolated from NK-92 show some contamination with nuclear material (small apoptotic bodies) but were free of other contaminating organelles, as shown in FIG. 3B.

Example 4

Cytotoxicity of EV/MV Preparations

The cytotoxicity of EV/MV preparations against Jurkat cells was tested using the culture conditions indicated in Table 1. Jurkat cells (2×10) were incubated in 170 μL medium (with ExoFree FBS) and 5, 15, or 30 μL of EV/MV preparation (with PBS to achieve total incubation volume of 200 μL) for 2 hours or 20 hours. Cytotoxicity was determined by propidium iodide (PI) assay, and data are expressed as the percent of cells that are PI positive (indicative of dead cells).

Figure 4:
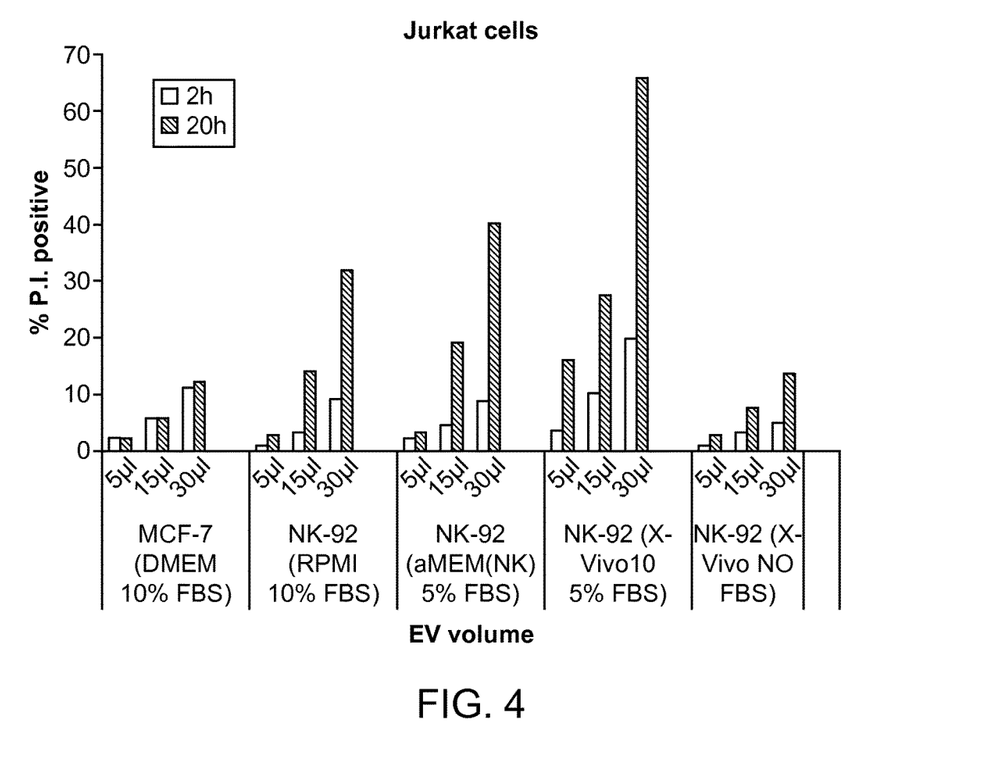
FIG. 4 shows the cytolytic activity of the NK-92 exosome/microvesicle preparation against Jurkat cells in a propidium iodide assay.

As shown in FIG. 4, EV/MV preparations from NK-92 cells, but not MCF-7 cells, have cytotoxic activity against Jurkat cells in vitro. Media composition changes the lytic potential of EV/MV, and the presence of serum in the growth medium stimulates production of lytic EV/MV by NK-92 cells.

What is claimed is:

1. A pharmaceutical composition comprising a pharmaceutically acceptable carrier and one or more isolated components from NK-92 cells, wherein the one or more components comprise exosomes and microvesicles, wherein the exosomes and microvesicles are tumoricidal and/or antimicrobial, and wherein the pharmaceutical composition is an injectable extended release formulation.

2. The pharmaceutical composition of claim 1, wherein the composition comprises a sterile aqueous solution.

3. The pharmaceutical composition of claim 2, wherein the sterile aqueous solution comprises a supernatant of a medium of NK-92 cells.

4. The pharmaceutical composition of claim 1, wherein the NK-92 cells comprise wild type NK-92 cells.

5. The pharmaceutical composition of claim 1, wherein the NK-92 cells comprise modified NK-92 cells.

6. The pharmaceutical composition of claim 1, wherein the NK-92 cells comprise NK-92 cells modified to express an Fc receptor, a cytokine, a cytokine receptor and/or a chimeric antigen receptor.

7. The pharmaceutical composition of claim 1, wherein the pharmaceutical composition is an injectable formulation.

8. The pharmaceutical composition of claim 7, wherein the pharmaceutical composition is formulated for subdermal or subcutaneous injection.

9. The pharmaceutical composition of claim 1, wherein the pharmaceutical acceptable carrier comprises a thickening agent.

10. The pharmaceutical composition of claim 1, wherein the pharmaceutical composition is a topical formulation.

11. The pharmaceutical composition of claim 10, wherein the topical formulation is liquid at room temperature and becomes a gel when applied to the body.

12. The pharmaceutical composition of claim 11, wherein the topical formulation comprises a poloxamer.

13. The pharmaceutical composition of claim 10, wherein the pharmaceutical composition is a cream or lotion.

14. The pharmaceutical composition of claim 1, wherein the pharmaceutical composition further comprises one or more cytokines.

15. The pharmaceutical composition of claim 14, wherein the one or more cytokines includes at least IL-2.

16. The pharmaceutical composition of claim 1, wherein the NK-92 cells are treated with at least one stimulatory agent prior to isolation of the one or more components.

17. The pharmaceutical composition of claim 16, wherein the at least one stimulatory agent is IL-15 and/or interferon gamma.

* * * * *